(12) United States Patent
Whiting et al.

(10) Patent No.: US 7,967,790 B2
(45) Date of Patent: Jun. 28, 2011

(54) HEMOSTASIS VALVE WITH IRIS SEAL

(75) Inventors: James S. Whiting, Los Angeles, CA (US); Werner Hafelfinger, Thousand Oaks, CA (US); Neal L. Eigler, Malibu, CA (US); John L. Wardle, San Clemente, CA (US)

(73) Assignee: Pacesetter, Inc., Sylmar, CA (US)

( * ) Notice: Subject to any disclaimer, the term of this patent is extended or adjusted under 35 U.S.C. 154(b) by 1 day.

(21) Appl. No.: 12/552,199

(22) Filed: Sep. 1, 2009

(65) Prior Publication Data

US 2011/0054405 A1    Mar. 3, 2011

(51) Int. Cl.
*A61M 5/178*    (2006.01)
(52) U.S. Cl. .................................. 604/167.03
(58) Field of Classification Search ............. 604/167.01, 604/167.03, 167.04, 167.06
See application file for complete search history.

(56) References Cited

U.S. PATENT DOCUMENTS

| | | | |
|---|---|---|---|
| 5,158,553 A * | 10/1992 | Berry et al. | 604/248 |
| 5,935,112 A | 8/1999 | Stevens et al. | |
| 6,458,103 B1 | 10/2002 | Albert et al. | |
| 6,695,820 B1 * | 2/2004 | Armstrong et al. | 604/256 |
| 7,172,580 B2 * | 2/2007 | Hruska et al. | 604/248 |
| 2005/0171479 A1 | 8/2005 | Hruska et al. | |

FOREIGN PATENT DOCUMENTS

WO    0024453    A2    5/2000
WO    0024453    A3    5/2000

* cited by examiner

*Primary Examiner* — Nicholas D Lucchesi
*Assistant Examiner* — Aarti B Berdichevsky

(57) ABSTRACT

A hemostasis valve is disclosed herein. The hemostasis valve may include an inner bushing, a rotation sleeve, an elastomeric sleeve, and a biasing element. The rotation sleeve may extend about the inner bushing and be rotationally displaceable relative to the inner bushing. The elastomeric sleeve may include a first end operably coupled to the inner bushing, a second end operably coupled to the rotation sleeve, and an iris valve portion. Rotation of the rotation sleeve relative to the inner bushing may cause the iris valve to transition from an open state to a closed state. The biasing element may act between the rotation sleeve and inner bushing to bias the iris valve towards at least one of a closed state or an open state.

8 Claims, 9 Drawing Sheets

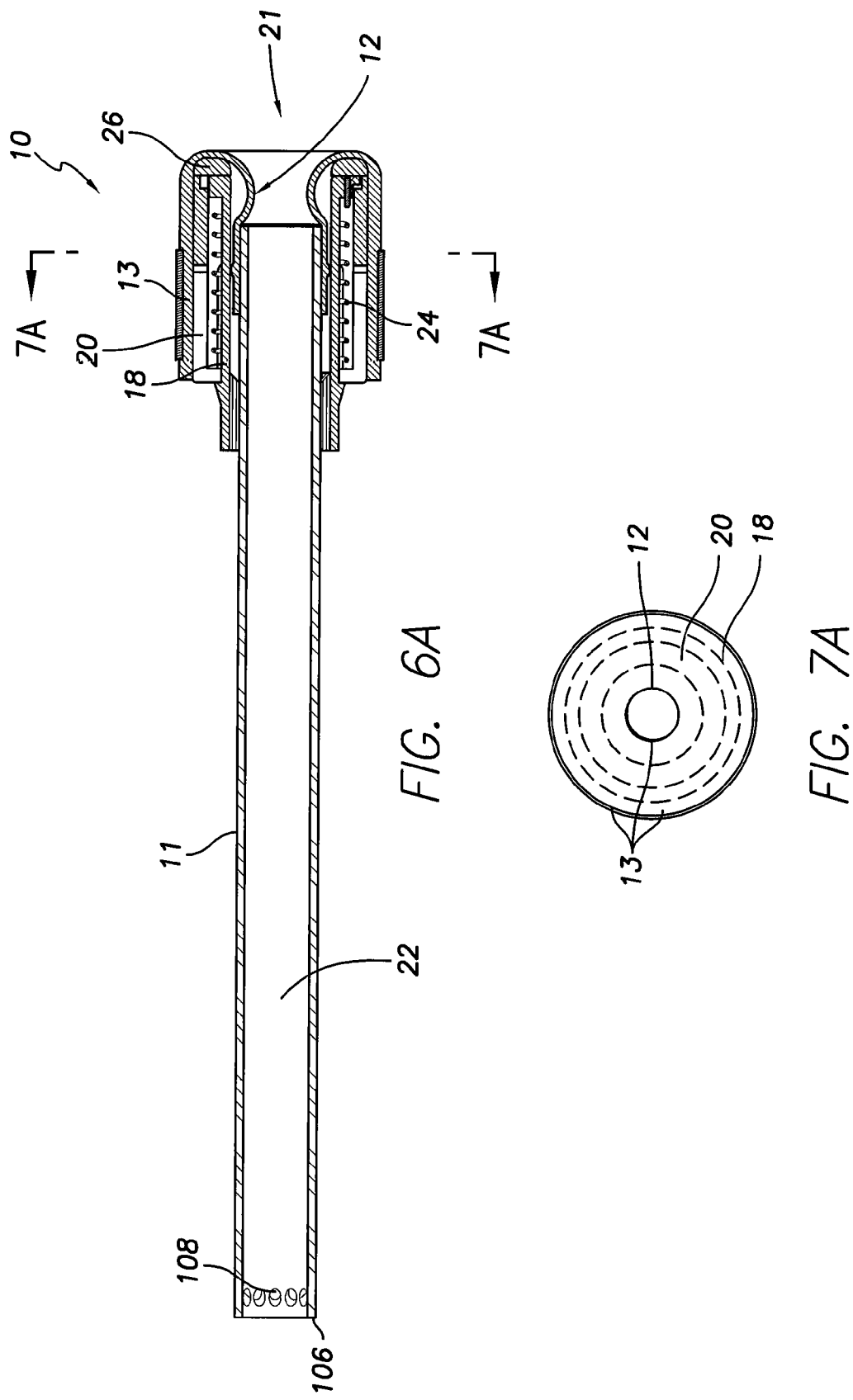

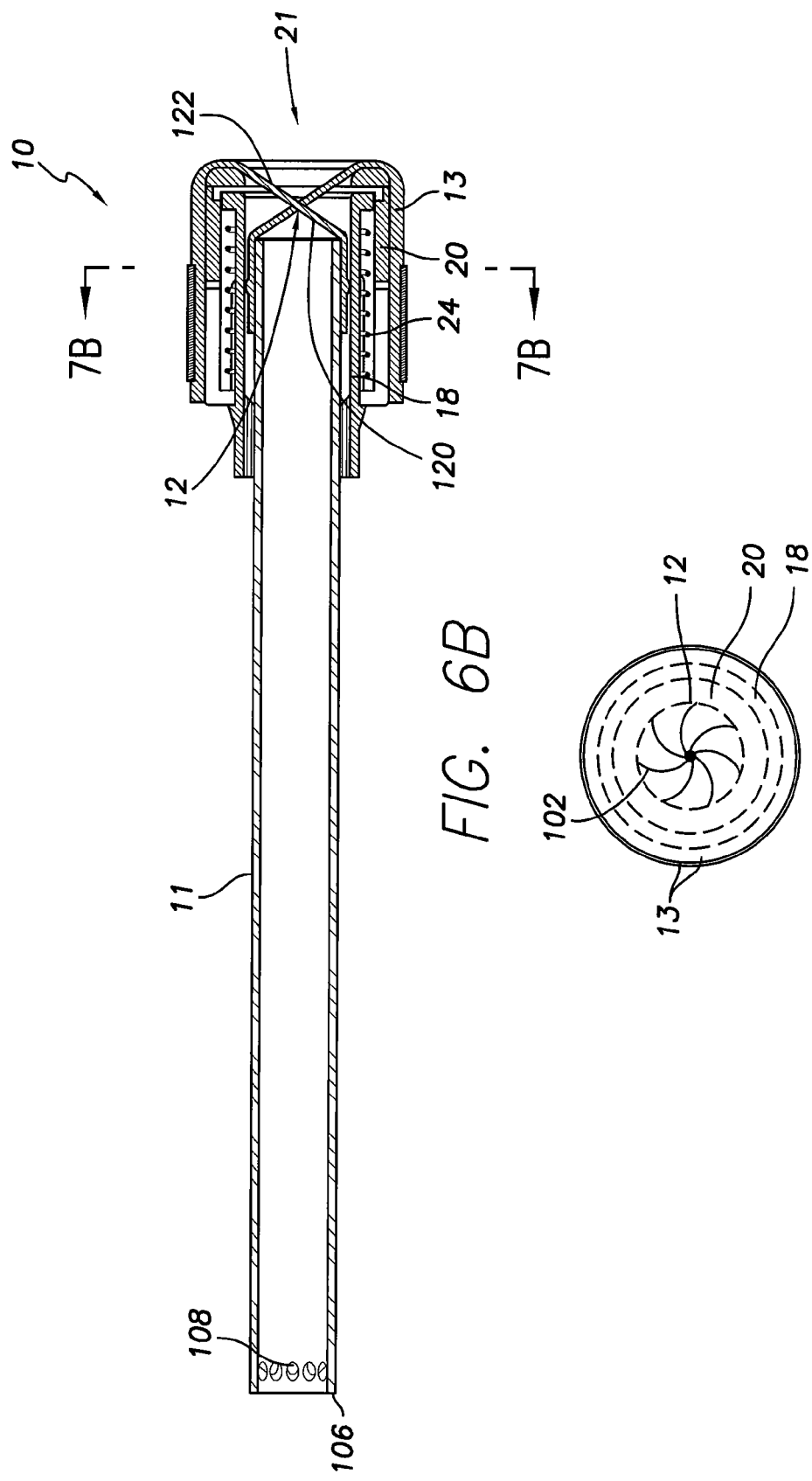

HEMOSTASIS VALVE WITH IRIS SEAL

FIELD OF THE INVENTION

The present invention relates to medical apparatus and methods. More specifically, the present invention relates to hemostasis valves and methods of using and manufacturing such valves.

BACKGROUND OF THE INVENTION

Hemostasis valves are employed in minimally invasive medical procedures such as, for example, the implantation of electrotherapy leads. Depending on the type of minimally invasive procedure occurring, the hemostasis valve may need to accommodate devices having a variety of diameters.

Unfortunately, hemostasis valves known in the art to provide acceptable sealing capability for a range of sizes that is not inconsequential often require two hands to operate. Also, such known hemostasis valves are biased to assume the open state, leading to a tendency to leak fluid when not desired.

There is a need in the art for a hemostasis valve that provides adequate sealing capabilities over a wide range of diameters for the devices that may be expected to be inserted through such valves. Also, there is a need in the art for a hemostasis valve that offers increased ease of use and improved sealing capability. Finally, there is a need in the art for a method of a method of manufacturing such a hemostasis valve.

BRIEF SUMMARY OF THE INVENTION

A hemostasis valve is disclosed herein. In one embodiment, the hemostasis valve includes an inner bushing, a rotation sleeve, an elastomeric sleeve, and a biasing element. The rotation sleeve may extend about the inner bushing and be rotationally displaceable relative to the inner bushing. The elastomeric sleeve may include a first end operably coupled to the inner bushing, a second end operably coupled to the rotation sleeve, and an iris valve portion. Rotation of the rotation sleeve relative to the inner bushing may cause the iris valve to transition from an open state to a closed state. The biasing element may act between the rotation sleeve and inner bushing to bias the iris valve towards at least one of a closed state or an open state.

In another embodiment, the hemostasis valve may include an inverted elastomeric sleeve forming an iris valve. The iris valve may include an arcuate portion that defines a most proximal opening of the hemostasis valve. The inverted elastomeric sleeve may form an arc that extends from a location inside the hemostasis valve to a location outside the hemostasis valve. At least a portion of the arc may form the iris valve. The arc may form approximately a half-circle.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 6A is a longitudinal cross section of the hemostasis valve and the catheter on which the hemostasis valve is mounted, wherein the seal is in a relaxed open state.

FIG. 6B is the same view as FIG. 6A, except the seal is in a collapsed sealed state.

FIG. 7A is an end view of the iris valve in the fully open state as viewed looking distally into the distal hemostasis valve opening as indicated by arrow A in FIG. 6A.

FIG. 7B is an end view of the iris valve in the fully closed state as viewed looking distally into the distal hemostasis valve opening as indicated by arrow A in FIG. 6B.

DETAILED DESCRIPTION

Figure 1:
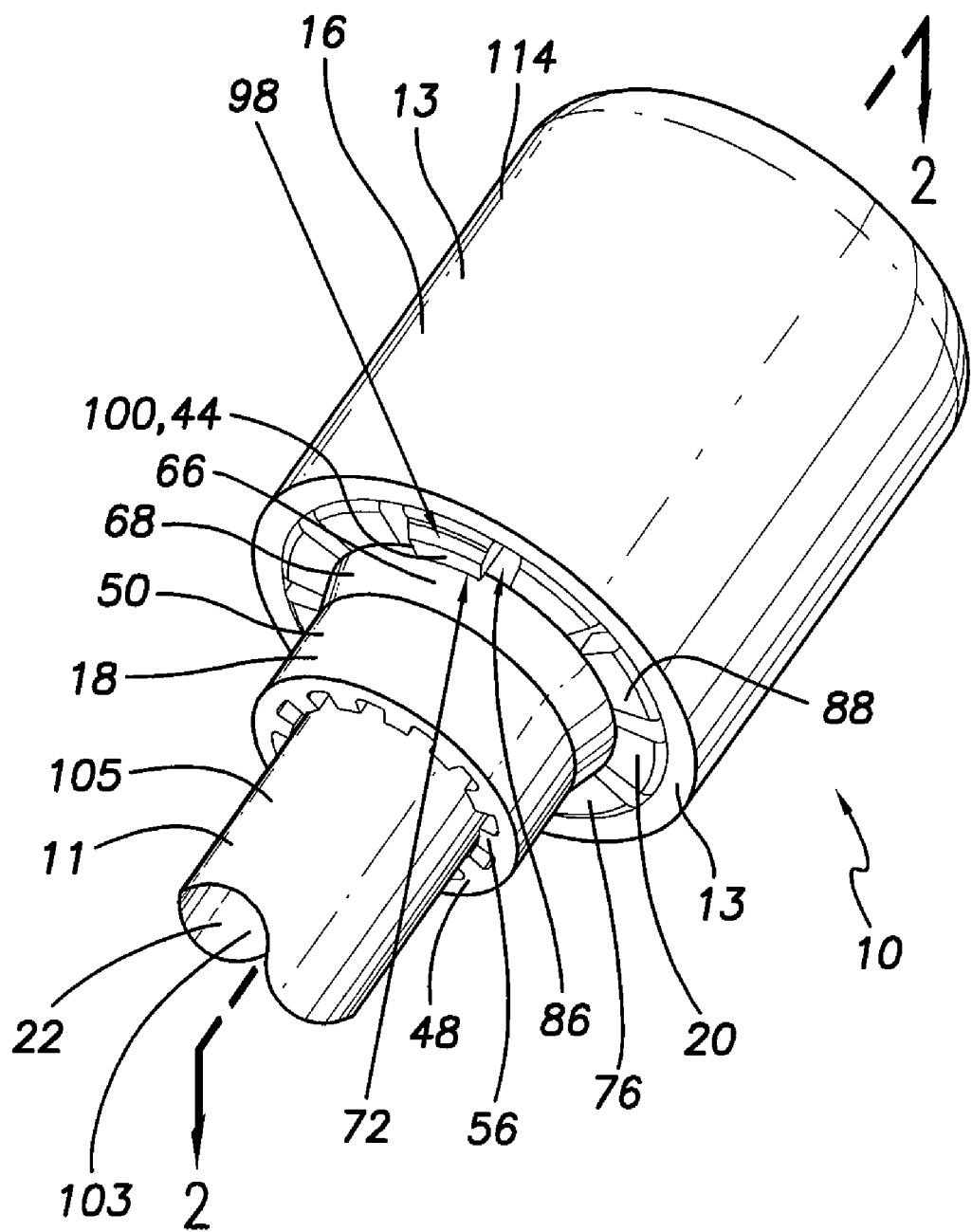
FIG. 1 is a distal isometric view of a hemostasis valve mounted on a proximal end of a catheter.

A hemostasis valve 10 is disclosed herein for use with a sheath or catheter 11 employed in a minimally invasive medical procedure, for example, in the delivery of an implantable electrotherapy lead. In one embodiment, the hemostasis valve 10 includes an iris valve 12 formed of an elastomeric membrane 13 having an inner end 14 and an outer end 16 respectively coupled to an inner bushing 18 and a rotation sleeve 20. The rotation sleeve 20 may be rotated relative to the inner bushing 18 to cause the iris valve 12 to transition between a fully closed state and a fully open state, thereby sealing or opening a proximal opening 21 of the hemostasis valve 10, the opening 21 providing access to the proximal end of the catheter lumen 22. In one embodiment, the hemostasis valve 10 may include a biasing feature 24 that causes the iris valve 12 to be biased to assume the closed state.

Figure 2:
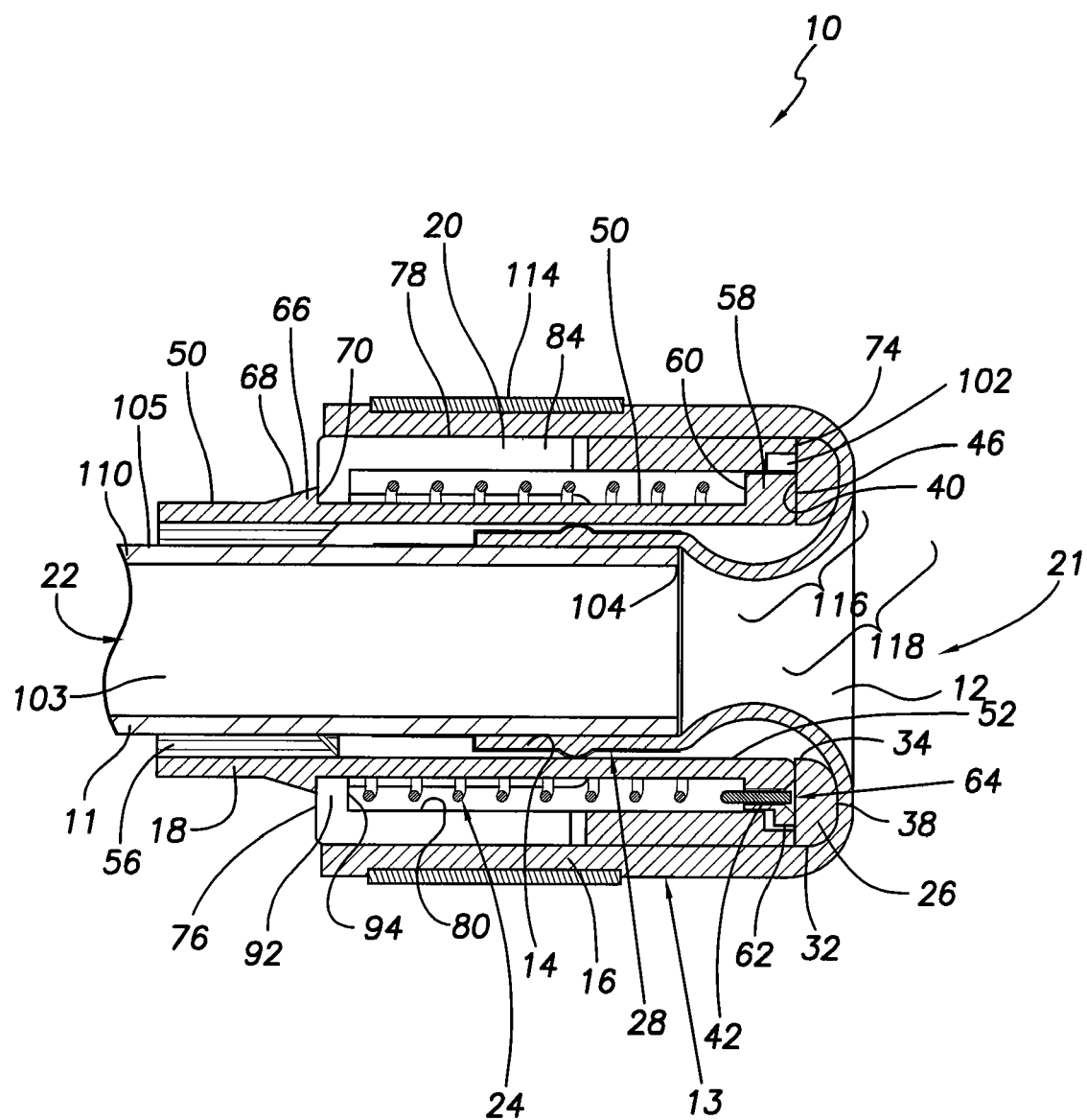
FIG. 2 is a longitudinal cross section of the hemostasis valve as taken along section line 2-2 in FIG. 1.
Figure 3:
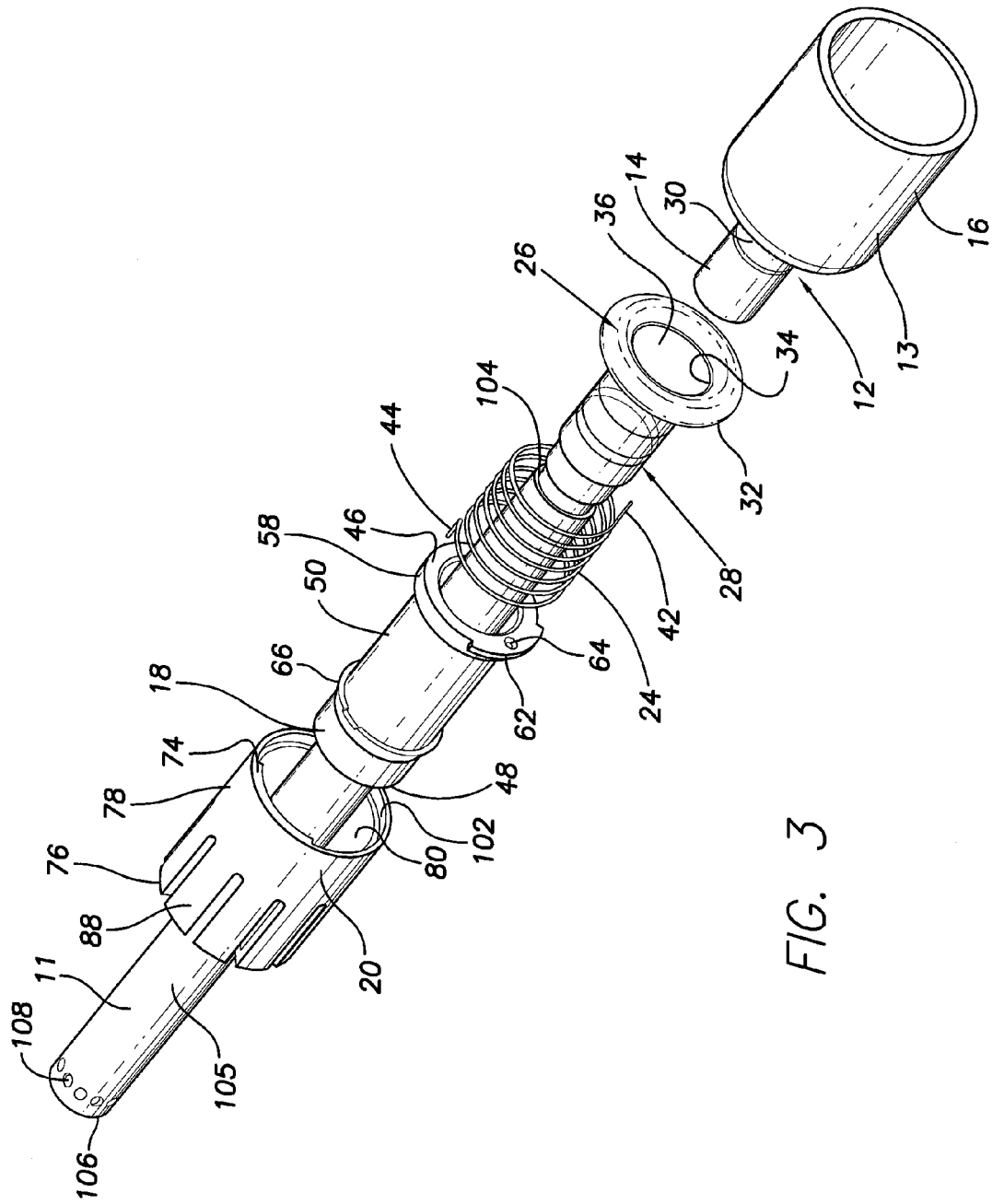
FIG. 3 is an exploded proximal isometric view of the hemostasis valve.

For a detailed discussion regarding the hemostasis valve 10, reference is made to FIGS. 1-3, which are, respectively, a distal isometric view of the hemostasis valve 10 mounted on a proximal end of the catheter 11, a longitudinal cross section of the hemostasis valve 10 as taken along section line 2-2 in FIG. 1, and an exploded proximal isometric view of the hemostasis valve 10. As indicated in FIGS. 1 and 2, in one embodiment, the hemostasis valve 10 may be configured to be mounted on the proximal end of a catheter 11. As most readily understood from FIG. 3, in one embodiment, the hemostasis valve 10 may include an elastomeric membrane 13, an end cap 26, a shrink tube 28, a biasing element 24, an inner bushing 18, and a rotation sleeve 20.

As illustrated in FIG. 3, in one embodiment, the elastomeric membrane 13 may include an inner end 14, an outer end 16, and a transition portion 30. The outer end 16 has a diameter that may be substantially larger than the diameter of the inner end 14. The transition portion 30 may join the inner end 14 and outer end 16 and, as can be understood from FIG. 2, may have an hour glass or bioconcave cross section when assembled into the hemostasis valve 10 and in an open state. The transition portion 30 may act as the iris valve 12 when the hemostasis valve 10 is operated. The elastomeric sleeve 13 may be formed of a low compression set elastomeric material such as, silicone rubber, nitrile, urethane, etc.

As depicted in FIG. 3, the end cap 26 may have a ring shape having an outer circumferential edge 32 and an inner circumferential edge 34 that defines a central opening 36. As shown in FIG. 2, the end cap 26 may have a proximal face 38 and a distal face 40. The proximal face 38 may be generally curved or arcuate as it extends between the inner edge 34 and outer edge 32, and the distal face 40 may be generally flat or planar between the inner edge 34 and the outer edge 32. The end cap 26 may be formed of low friction materials such as, for example, polytetrafluoroethylene ("PTFE"), or etc. Surface lubricants, e.g., silicone oil can be added to the surfaces to enchase lubricity and device function As shown in FIG. 3, the shrink tube 28 may be cylindrical in shape and include proximal and distal ends. The shrink tube 28 may be formed of materials, such as, for example, fluorinated ethylene propylene ("FEP"), polyester, kynar, etc.

As illustrated in FIG. 3, in one embodiment, the biasing element 24 may be in the form of a helically wound spring 24 having a proximal end tip 42 and a distal end tip 44 that are respectively coupled to the inner bushing 18 and the rotation sleeve 20, as described below. The spring 24 may be formed of materials, such as, for example, stainless steel, nitinol, etc. The biasing element may provide a torsion and compression force between the inner bushing 18 and the rotation sleeve 20.

As indicated in FIG. 3, the inner bushing 18 may have a generally cylindrical configuration, a proximal end face 46, and a distal end face 48. As shown in greater detail in FIGS. 4A and 4B, which are, respectively, distal and proximal isometric views of the inner bushing 18, the inner bushing 18 may include an outer circumferential surface 50 and an inner circumferential surface 52 that extend between the proximal end face 46 and the distal end face 48. The inner circumferential surface 52 may define an opening 54 that extends through the inner bushing 18. The inner circumferential surface 52 may include a series of spaced-apart longitudinally extending keys 56 that radially extend into the opening 54 over approximately the distal quarter or third of the length of the inner circumferential surface 52, the distal end faces of the keys 56 being generally coextensive with the distal end face 48. In one embodiment, the keys 56 are to keep part thickness uniform for effective molding. The keys may also provide a cavity in which adhesive may reside for assembly.

Figure 4A:
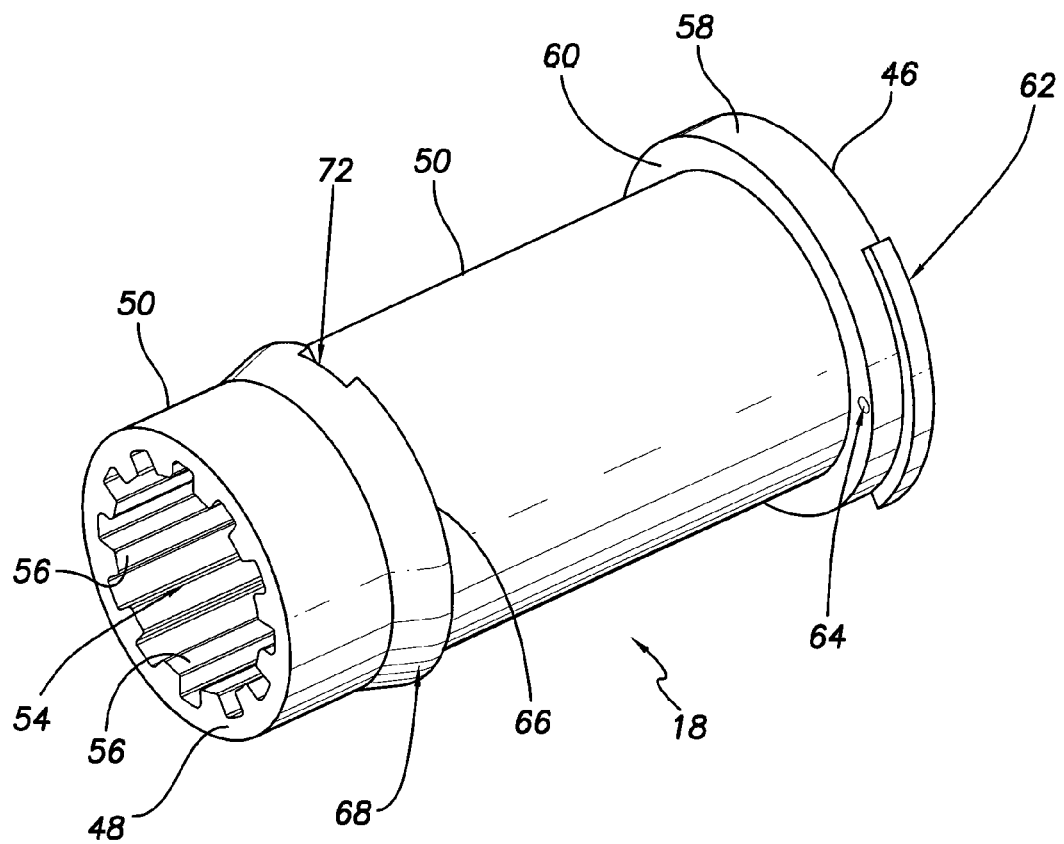
FIG. 4A is a distal-side isometric view of the inner bushing of the hemostasis valve.
Figure 4B:
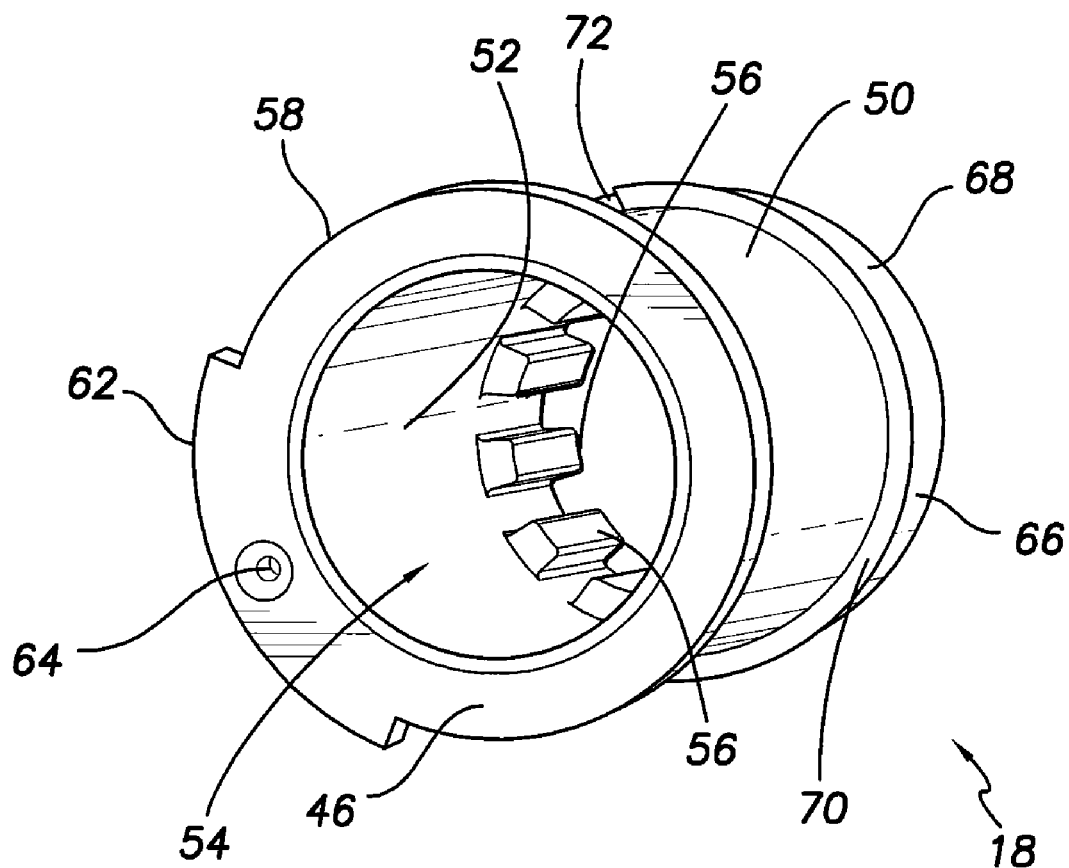
FIG. 4B is a proximal isometric view of the inner bushing depicted in FIG. 4A.

As depicted in FIGS. 4A and 4B, the outer circumferential surface 50 of the inner bushing 18 may include a proximal flange 58 radially extending from the outer circumferential surface 50 and including a distal end face 60 and proximal end face that may be coextensive with the proximal end face 46. A stop flange 62 may extend from the outer circumferential surface of the proximal flange 58 over approximately a quarter to a third of the circumference of the proximal flange 58. A hole 64 may extend through the proximal flange 58 in the vicinity of the stop flange 62 and may receive the proximal end tip 42 of the biasing element 24.

As shown in FIGS. 4A and 4B, the outer circumferential surface 50 of the inner bushing 18 may also include a tapered stop 66 radially extending from the outer circumferential surface 50 and including a sloped distal face 68 and proximal face 70 generally perpendicular to the outer circumferential surface 50. The tapered stop 66 may also includes a notch 72 defined in the proximal face 70. The notch 72 may be relatively small in its circumferential length relative to the circumference of the stop 66. Also, the notch 72 may be circumferentially offset from the flange 62. The inner bushing 18 may be molded or machined of materials with good spring properties, such as, for example, Delrin, or polycarbonate.

As indicated in FIG. 3, the rotation sleeve 20 may have a generally cylindrical configuration, a proximal end face 74, and a distal end face 76. As shown in greater detail in FIGS. 5A and 5B, which are, respectively, distal and proximal isometric views of the rotation sleeve 20, the rotation sleeve 20 may include an outer circumferential surface 78 and an inner circumferential surface 80 that extend between the proximal end face 74 and the distal end face 76. The inner circumferential surface 80 may define an opening 82 that extends through the rotation sleeve 20. The wall 84 of the rotation sleeve 20 between the inner circumferential surface 80 and outer circumferential surface 78 may include a series of spaced-apart longitudinally extending slots 86 that define longitudinally extending legs 88 that extend over approximately the distal half of the length of the rotation sleeve 20, the distal end faces of the legs 88 being generally coextensive with the distal end face 76. Legs 88 are designed to spring outward over sloped distal face 68 to permit assembly; once assembled, the legs 88 snap back and prevent proximal migration of the component. The distal ends 90 of the legs 88 are free and may define a radially inward extending segmented flange 92 having a distal face that is generally coextensive with the distal end face 76 and a proximal face 94 that is generally perpendicular to the inner circumferential surface 80. The proximal ends 96 of the legs 88 extend into the proximal, non-segmented portion of the rotation sleeve 20.

Figure 5A:
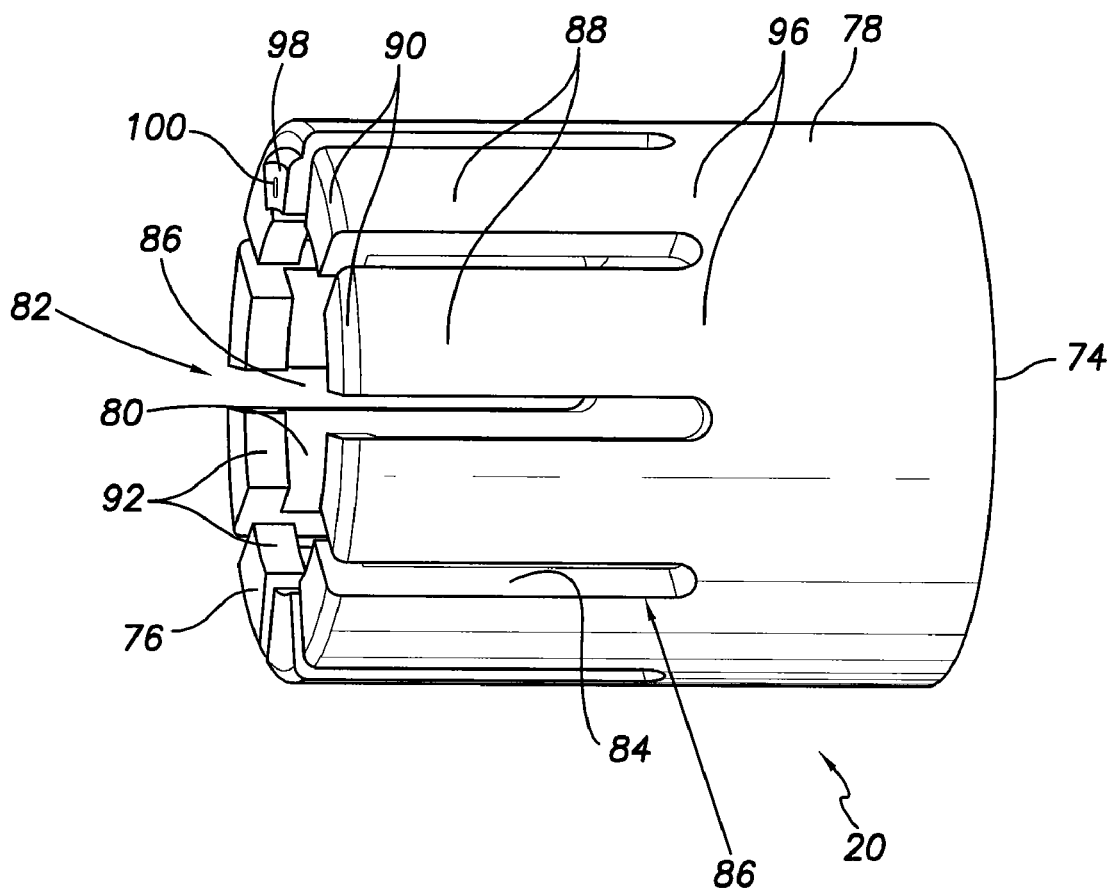
FIG. 5A is distal-side isometric view of the rotation sleeve of the hemostasis valve.
Figure 5B:
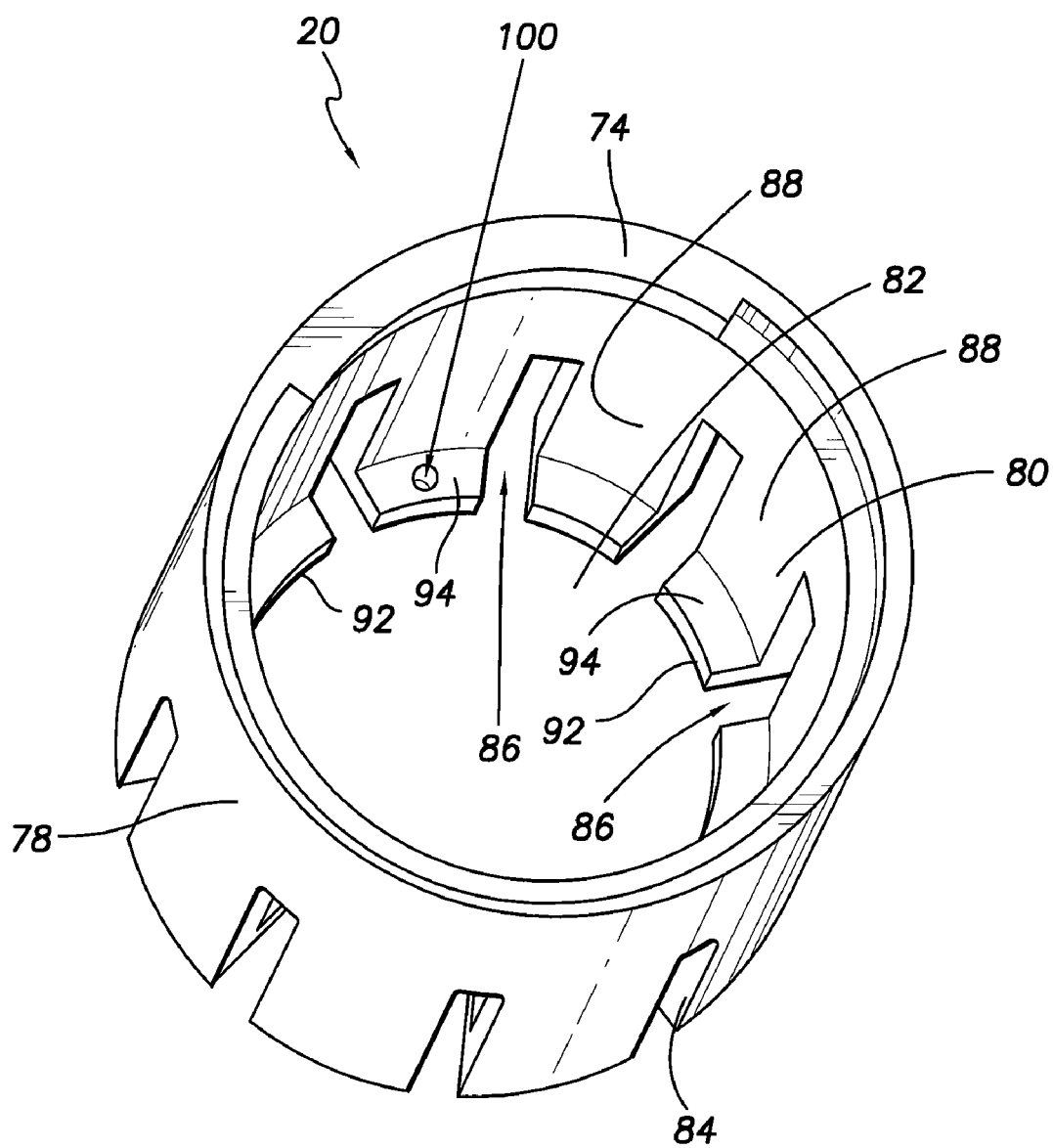
FIG. 5B is a proximal isometric view of the rotation sleeve depicted in FIG. 5A.

As indicated in FIG. 5A, a distal end face of one of the legs 88 my include a tab or bump 98 projecting distally from the leg distal end face such that the distal end face is not coextensive with the end face 76. As shown in FIGS. 5A and 5B, a hole 100 may extend through the bump 98 and leg flange 92 and may receive the distal end tip 44 of the biasing element 24.

As illustrated in FIG. 5B, the proximal end face 74 of the rotation sleeve 20 may include a groove 102 defined in proximal end face 74 and radially extending outward from the inner circumferential surface 80 to approximately the midpoint of the thickness of the rotation sleeve wall 84. The groove 102 may have a circumferential length that is approximately three quarters of the circumference of the rotation sleeve wall 84. As described below, the groove 102 may receive the stop flange 62 to limit the rotational displacement of the rotation sleeve 20 about the inner bushing 18.

As indicated in FIG. 3, the catheter 11 may include a central lumen 22 (see FIGS. 1 and 2), an inner circumferential surface 103 defining the lumen 22, a proximal end 104, an outer circumferential surface 105, and a distal end 106. The inner circumferential surface 103 and the outer circumferential surface 105 extend between the proximal end 104 and the distal end 106. The distal end 106 may include flush ports 108 extending through the catheter wall 110 (see FIG. 2).

When the above-described components of the hemostasis valve 10 are assembled together to form the assembled hemostasis valve 10 as shown in FIGS. 1 and 2, the catheter proximal end 104 is received in the inner end 14 of the elastomeric sleeve 13 such that the inner end 14 conforms snuggly about the outer circumferential surface 105 of the catheter 11. The shrink tube 28 extends about the outer circumferential surface of the inner end 14 of the elastomeric sleeve 13 extending about the catheter proximal end 104. The shrink tube 28 also extends about the outer circumferential surface 105 of the catheter 11 over a region distal of the distal edge of the inner end 14 of the elastomeric sleeve 13. A heat shrink process is used to cause the heat shrink tube 28 to conform about the outer circumferential surfaces of the elastomeric sleeve and the catheter, squeezing and capturing the inner end 14 of the elastomeric sleeve 13 to the outer circumferential surface 105 of the distal end of the catheter 11.

As illustrated in FIG. 2, the catheter distal end 104, inner end 14, and shrink tube 28 combination is received in the inner bushing opening 54 (shown in FIGS. 4A and 4B) such that the inner circumferential surface 52 (shown in FIG. 4B) extends about and is parallel to the outer circumferential surfaces of the catheter, inner end 14 and heat shrink tube. The catheter distal end 104 is distally recessed within the inner bushing opening 54 so the proximal face 46 of the inner bushing 18 is proximally offset from the catheter distal end 104. The surfaces of the keys 56 of the inner bushing 18 engage the catheter outer circumferential surface 105 distal of the shrink tube distal edge. The engagement between the keys 56 and the catheter outer circumferential surface 105 may be a friction or clearance fit arrangement and/or employ an adhesive or weld such that the inner bushing 18 will not displace relative to the catheter 11. For example, in one embodiment, an adhesive is applied to circumferential surface 105 and squeezes out through keys 56. This permanently retains the shrink tube.

As depicted in FIG. 2, the inner bushing 18 is received in the rotation sleeve opening 82 such that the inner circumferential surface 80 extends about and is parallel to the outer circumferential surface 50 of the inner bushing 18. The proximal end face 74 of the rotation sleeve 20 is generally even with respect to proximal location relative to the proximal end face 46 of the inner bushing 18. The stop flange 62 is located in the groove 102 of the rotation sleeve 20 such that the rotation of the rotation sleeve 20 is limited to less than a full 360 rotation about the inner bushing 18. In one embodiment, wherein the groove 102 has a length that is approximately three quarters of the circumference of the rotation sleeve 20 and the stop flange 62 has a length that is approximately one quarter of the circumference of the inner bushing 18, the rotation of the rotation sleeve 20 relative to the inner bushing 18 may be limited to approximately 180 degrees of rotation.

As shown in FIG. 2, the inner circumferential surface of the rotation sleeve flange 92 contacts the inner bushing outer circumferential 50. As illustrated in FIGS. 1 and 2, the distal end face 76 of the rotation sleeve 20 rests against the proximal face 70 of the inner bushing 18 when the bump 98 resides in the notch 72. As discussed below, the bump 98 residing in the notch 72 may be used to prevent the rotation sleeve 20 from rotating about the inner bushing 18 unless some positive action is taken to disengage the bump 98 from the notch 72.

As can be understood from FIGS. 1-5B, the biasing element 24 may extend about the inner bushing outer circumferential surface 50 between the inner bushing proximal flange 58 and the rotation sleeve distal flange 92. The proximal end 42 of the biasing element 24 is received in the flange hole 64 of the inner bushing 18, and the distal end 44 of the biasing element 24 is received in the flange hole 100 of the rotation sleeve 20. Thus, the biasing element 24 may exert a torsion force to the rotation sleeve 20 relative to the inner bushing 18 such that the rotation sleeve 20 is caused to rotate in a certain direction about the inner bushing 18. For example, the biasing element 24 may bias the rotation sleeve 20 to rotate about the inner bushing 18 so as to cause the iris valve 12 to assume a closed state. In other embodiments, the biasing element may be configured to cause the opposite result, i.e., the iris valve 12 assuming an open state. The biasing element 24 may exert a compression force to the rotation sleeve 20 relative to the inner bushing 18 such that the rotation sleeve distal flange 92 is biased distally-proximally from the inner bushing proximal flange 58. This compressive force of the spring 24 maintains the bump 98 within the notch 72 once the bump 98 is received in the notch 72 and until a proximally oriented force of sufficient magnitude is exerted against the rotation sleeve 20 to proximally displace the rotation sleeve against the compressive biasing force of the spring 24, thereby allowing the bump 98 to clear the notch 72 as the taped flange proximal face 70 and rotation sleeve distal face 76 proximally-distally separate.

As indicated in FIG. 2, the flat distal face 40 of the end cap ring 26 abuts against both the inner bushing proximal face 46 and the rotation sleeve proximal face 74. The outer end 16 of the elastomeric sleeve 13 extends over the proximal rounded face 38 of the ring 26. The ring 26, which may be formed of a low-friction material, may act as a low friction bearing surface between the various surfaces of the inner bushing, rotation sleeve and material 13 that displace against each other when the rotation sleeve 20 is rotated relative to the inner bushing 18. The elastomeric sleeve 18 is folded back on itself and has a smaller inside diameter than the rotation stop. This ensures that there is a compressive retaining force between these mating components.

As indicated in FIGS. 1 and 2, the outer end 16 of the elastomeric sleeve 13 exits the inner bushing opening 54, extends about the ring proximal face 38, and extends over the rotation sleeve outer circumferential surface 78 in a snug conforming fit. In one embodiment, the material 13 is shrunk to the rotation sleeve outer circumferential surface 78 via a shrink tube 200 or via other mechanisms or methods. The iris valve 12, when in a fully open state, may have an hour glass or bioconcave shape.

As can be understood from FIGS. 1-5B, in one embodiment, the elastomeric sleeve inner end 14, shrink tube 28 and catheter distal end 104 are assembled as described above. The catheter 11 is inserted distal end first through the end cap ring opening 36 until the ring 26 extends about the proximal edge of the iris valve 12 as shown in FIG. 2. The catheter 11 is inserted distal end first through the inner bushing opening 54 until the catheter proximal end 104 is positioned inside the inner bushing 18 and the ring distal face 40 and inner bushing proximal face 46 abut as indicated in FIG. 2. The spring 24 may be displaced proximally over the catheter 11 and inner bushing 18 so the spring expands over the inner bushing tapered flange 66 to reside between the tapered flange 66 and the proximal flange 58 as shown in FIG. 2. The spring proximal end 42 is received in the bushing flange hole 64. The rotation sleeve 20 may be displace proximally over the catheter 11, inner bushing 18 and spring 24 until the rotation sleeve proximal face 74 abuts the ring distal face 40 as shown in FIG. 2. In doing so, the spring distal end 44 is received in the sleeve flange hole 100, and the sleeve flange 92 expands outward via the flexibility afforded by the legs 88 as the flange 92 rides over the tapered flange 66 and drops into place proximal of the tapered flange proximal face 70, as indicated in FIG. 2. The outer end 16 of the elastomeric sleeve 13 is pulled over the outer circumferential surface 78 of the rotation sleeve 20 as indicated in FIGS. 1 and 2.

For a discussion of the operation of the hemostasis valve 10, reference is made to FIGS. 6A and 6B, which are longitudinal cross sections of the hemostasis valve 10 and catheter 11 on which the hemostasis valve 10 is mounted, wherein the seal 12 is in a relaxed open state and a collapsed state, respectively. In one embodiment, the hemostasis valve 10 is biased by the spring 24 such that the iris valve 12 is biased closed as indicated in FIG. 6B, the physician having to physically rotate the rotation sleeve 20 relative to the inner bushing 18 in order to overcome the biasing force of the spring 24 and cause the iris valve 12 to open as shown in FIG. 6A. In such an embodiment, to maintain the rotation sleeve 20 rotated relative to the inner bushing 18 so as to maintain the iris valve 12 in the open state as depicted in FIG. 6A, once the rotation sleeve 20 is fully rotated relative to the inner bushing 18, the bump 98 may be received in the notch 72 as shown in FIG. 1. The compressive force of the spring 24 will cause the bump to remain in the notch, and the bump/notch engagement will prevent the torsion force of the spring 24 from rotating the rotation sleeve relative to the inner bushing such that the iris valve 12 closes. To cause the bump 98 to disengage the notch 72, a proximal force may be applied to the bump, causing the bump and/or rotation sleeve 20 to proximally displace relative to the notch 72. Once the bump/notch engagement ceases to exist, the spring 24 may bias the rotation sleeve 20 to rotate relative to the inner bushing 18 such that the iris valve 12 closes as depicted in FIG. 6B. Advantageously, this aspect of the valve allows the flick of a finger to close the valve instantly as the unrestrained spring will automatically close the valve. A few seconds lost in closing the valve could result in a back flow of air which could cause a fatality, and the valve's configuration and operation avoids such as situation by being capable of being closed instantly via a flick of a finger. While the preceding discussion is directed to the hemostasis valve 10 being biased to close the iris valve 12 and the bump/notch engagement is configured to maintain the iris valve 12 open, the reverse may be true in other embodiments. For example, the hemostasis valve 10 being biased to open the iris valve 12 and the bump/notch engagement is configured to maintain the iris valve 12 closed.

As can be understood from FIG. 6A and from FIG. 7A, which is an end view of the iris valve 12 as viewed looking distally into the opening 21 as indicated by arrow A in FIG. 6A, the iris valve 12 when in an open state may have a generally uniform circular opening. As can be understood from FIG. 6B and from FIG. 7B, which is an end view of the iris valve 12 as viewed looking distally into the opening 21 as indicated by arrow A in FIG. 6B, the iris valve 12 when in a closed, sealed state is in a twisted condition that causes the wall of the elastomeric sleeve 13 in the region of the iris valve 12 to twist or wind about itself such that the resulting twist seams 102 created in the iris valve 12 helically wind through the iris valve region.

As the hemostasis valve 10 is configured to be biased into a closed state and may be held in the open state by the bump/notch engagement, the hemostasis valve 10 may be operated with a single hand by causing a proximal force to be exerted against the bump 98 to cause the bump to clear the notch 72 (e.g., by causing the bump 98 to abut against a guidewire or guiding catheter during a lead implantation procedure), the spring 24 then biasing the iris valve 12 closed.

As can be understood from FIG. 2, in one embodiment, the elastomeric sleeve 13 extends uninterrupted from extending about the catheter proximal end 104 to extend about the rotation sleeve outer circumferential surface 78. Thus, the elastomeric sleeve 13 may form both the iris seal 12 and a gripping surface 114 of the hemostasis valve 10 or, more specifically, the rotation sleeve 20.

As indicated in FIG. 2, the elastomeric sleeve 13 is folded back on itself or inverted. Partially as a result of the inverted configuration of the elastomeric sleeve 13, the arc 116 formed in the elastomeric sleeve and forming at least a portion of the iris seal 12 may extend from the catheter proximal end 104, about the ring arcuate surface 38, and to approximately the interface between the ring distal planar face 40 and the rotation sleeve proximal face 74. Thus, the arc 116 may extend sufficiently far so as to be approximately a half-circle between the catheter proximal end 104 and the interface between the ring 26 and the rotation sleeve 20.

As shown in FIG. 2, the arc 116 of the elastomeric sleeve 13 may form the most proximal end or boundary of the hemostasis valve 10. Also, the arc 116 of the elastomeric sleeve 13 may form or define the proximal opening 21 leading into the hemostasis valve 10 leading to the iris valve 12.

As depicted in FIG. 2, the arcuate portion 118 of the iris valve 12 may begin at approximately the most proximal end or boundary of the hemostasis valve 10 and extend to the catheter distal end 104. Also, the arcuate portion 118 of the iris valve 12 may form or define the proximal opening 21 leading into the hemostasis valve 10 leading to the iris valve 12.

As can be understood from FIGS. 6A-7B, the hemostasis valve 10 can be operated to effect full opening or full closure of the circular opening of the iris valve 12. The hemostasis valve 10 can also be operated to effect variable constriction of the circular opening of the iris valve 12 to engage the circumference of a medical device inserted through the circular opening so as to prevent fluid flow and/or air from passing around the circumference of the medical device.

As illustrated in FIGS. 6B and 7B, the constriction of the iris valve 12 may be the combined result of a radial reduction in circular opening and a folding of the in the wall of the elastomeric sleeve 13. In part due to the elastomeric sleeve 13 being folded back on itself or inverted, more tension is caused in the folds of the elastomeric sleeve 13 when twisted in the region of the iris valve 12, thereby creating a more effective sealing of the iris seal 12. Furthermore, the configuration of the distal cone 120 formed by the iris seal when fully closed, as depicted in FIG. 6B, allows back pressure to increase the sealing effect of the iris seal 12.

As shown in FIG. 6B, when the iris seal 12 is fully closed, the resulting distal cone 120 and proximal cone 122 formed by the iris seal 12 may each be generally uniform in their respective configurations as a result of the arcuate configuration 116, 118 of the folded or inverted configuration of the elastomeric sleeve 13. Thus, the iris valve 12 tends to be uniformly constricted when in a closed state. Also, the proximal cone 122 tends to extend distally to its distal apex from generally a most proximal edge of boundary of the hemostasis valve 10 and the most proximal edge of the proximal opening 21.

Although the present invention has been described with reference to preferred embodiments, persons skilled in the art will recognize that changes may be made in form and detail without departing from the spirit and scope of the invention.

What is claimed is:

1. A hemostasis valve comprising:
   an inner bushing;
   a rotation sleeve extending about the inner bushing and rotationally displaceable relative to the inner bushing;
   an elastomeric sleeve including a first end operably coupled to the inner bushing, a second end operably coupled to the rotation sleeve, and an iris valve portion, wherein rotation of the rotation sleeve relative to the inner bushing causes the iris valve to transition from an open state to a closed state;
   a biasing element acting between the rotation sleeve and inner bushing to bias the iris valve towards at least one of a closed state or an open state; and
   an engagement arrangement between the rotation sleeve and the inner bushing that, when engaged, prevents the biasing element from rotating the rotation sleeve relative to the inner bushing.

2. The hemostasis valve of claim 1, wherein the biasing element provides a proximal-distal force that maintains the engagement of the engagement arrangement.

3. The hemostasis valve of claim 2, wherein the engagement arrangement includes a notch on the inner bushing and a bump on the rotation sleeve that is received in the notch.

4. A hemostasis valve comprising:

an inner bushing;

rotation sleeve extending about the inner bushing and rotationally displaceable relative to the inner bushing;

an elastomeric sleeve including a first end operably coupled to the inner bushing, a second end operably coupled to the rotation sleeve, and an iris valve portion, wherein rotation of the rotation sleeve relative to the inner bushing causes the iris valve to transition from an open state to a closed state;

a biasing element acting between the rotation sleeve and inner bushing to bias the iris valve towards at least one of a closed state or an open state; and a low friction ring including a distal face interfacing with at least one of a proximal end face of the inner bushing or a proximal end face of the rotation sleeve.

5. The hemostasis valve of claim 4, wherein the elastomeric sleeve extends over a proximal face of the low friction ring as the elastomeric sleeve extends between the first end and the second end.

6. The hemostasis valve of claim 4, wherein the elastomeric sleeve forms a most proximal surface of the hemostasis valve.

7. The hemostasis valve of claim 4, wherein the elastomeric sleeve defines a proximal opening of the hemostasis valve leading to the iris valve.

8. The hemostasis valve of claim 4, wherein the elastomeric sleeve further includes a grip portion extending over an outer surface of the rotation sleeve.

* * * * *